United States Patent
Ho et al.

(10) Patent No.: US 11,709,128 B2
(45) Date of Patent: Jul. 25, 2023

(54) OPTICAL DETECTION APPARATUS

(71) Applicant: Lextar Electronics Corporation, Hsinchu (TW)

(72) Inventors: Fu-Han Ho, Hsinchu (TW); Kai-Hung Cheng, Hsinchu (TW)

(73) Assignee: Lextar Electronics Corporation, Hsinchu (TW)

( * ) Notice: Subject to any disclaimer, the term of this patent is extended or adjusted under 35 U.S.C. 154(b) by 132 days.

(21) Appl. No.: 17/244,912

(22) Filed: Apr. 29, 2021

(65) Prior Publication Data
US 2022/0268690 A1 Aug. 25, 2022

(30) Foreign Application Priority Data
Feb. 22, 2021 (CN) .......................... 202110199183.4

(51) Int. Cl.
*G01N 21/17* (2006.01)

(52) U.S. Cl.
CPC ....... *G01N 21/17* (2013.01); *G01N 2201/062* (2013.01); *G01N 2201/08* (2013.01)

(58) Field of Classification Search
CPC ............. G01N 21/17; G01N 2201/062; G01N 2201/08; A61B 5/00
See application file for complete search history.

(56) References Cited

U.S. PATENT DOCUMENTS

| | | | |
|---|---|---|---|
| 8,558,161 B2 * | 10/2013 | Ong | G02B 19/008 250/221 |
| 9,752,925 B2 | 9/2017 | Chu et al. | |
| 10,128,401 B2 * | 11/2018 | Chen | H04N 1/00734 |
| 10,281,611 B2 * | 5/2019 | Uedaira | G01V 8/12 |
| 10,551,499 B2 | 2/2020 | Hsu et al. | |
| 10,610,159 B2 | 4/2020 | Eletr et al. | |
| 2015/0234941 A1 | 8/2015 | Xiong et al. | |
| 2019/0377858 A1 | 12/2019 | He et al. | |
| 2020/0096691 A1 | 3/2020 | Nagamoto et al. | |

FOREIGN PATENT DOCUMENTS

TW    I547850 B    9/2016

* cited by examiner

*Primary Examiner* — Seung C Sohn
(74) *Attorney, Agent, or Firm* — CKC & Partners Co., LLC

(57) ABSTRACT

An optical detection apparatus includes a substrate, a light source, a light sensor, a light-guiding structure. The substrate has a top surface. The light source on the top surface is configured to generate detection light toward an object over the light source. The light sensor is located on the top surface. The light-guiding structure is above the top surface and at least partially above the light source. A central axis of the light-guiding structure is vertical to the top surface, and the light source and the light sensor are at opposite sides relative to the central axis. The light-guiding structure is configured to deflect the detection light from one of the opposite sides at which the light source is located to another one of the opposite side at which the light sensor is located, such that the detection light reflected by the object moves toward the light sensor.

15 Claims, 10 Drawing Sheets

OPTICAL DETECTION APPARATUS

CROSS-REFERENCE TO RELATED APPLICATION

This application claims priority to China Application Serial Number 202110199183.4, filed Feb. 22, 2021, which is herein incorporated by reference in its entirety.

BACKGROUND

Field of Invention

The present invention relates to an optical detection apparatus.

Description of Related Art

The medical testing technology has already progressed from invasive testing to non-invasive testing due to the advancement of science and technology.

In the process of detection, optical principles are used to detect a human body by some detection devices, and consumers always take the convenience of the optical detection devices in account. If the optical detection device is too large, it is unfavorable for the user to carry or wear. In addition, the manufacturers would like to show users new experience which is different from the existing optical detection devices, so as to attract more customers.

Therefore, how manufacturers can provide an optical detection device that can be miniaturized and innovative concepts for enhancing the convenience of use and product competitiveness has become one of the important issues.

SUMMARY

The invention provides an optical detection apparatus which includes a substrate, a light source, a light sensor, and a light-guiding structure. The substrate has a top surface. The light source on the top surface is configured to generate detection light toward an object over the light source. The light sensor is located on the top surface. The light-guiding structure is above the top surface and at least partially above the light source. A central axis of the light-guiding structure is vertical to the top surface, and the light source and the light sensor are at two opposite sides of the central axis. The light-guiding structure is configured to deflect the detection light from one of the two opposite sides at which the light source is located to the other one of the two opposite sides at which the light sensor is located, such that the detection light reflected by the object moves toward the light sensor.

In some embodiments of the present disclosure, the light-guiding structure includes a light-guiding convex portion which has a light incident surface. The light incident surface is inclined with respect to the central axis and configured for receiving the detection light.

In some embodiments of the present disclosure, the light-guiding structure comprises a cone-shaped light-guiding convex portion.

In some embodiments of the present disclosure, the light-guiding structure comprises a circular-arc shaped light-guiding convex portion.

In some embodiments of the present disclosure, the light-guiding structure comprises a column portion and a curved convex portion under the column portion.

In some embodiments of the present disclosure, the light-guiding structure comprises a column portion and a cone portion under the column portion.

In some embodiments of the present disclosure, the light-guiding structure includes a light-guiding convex portion and a lower recess portion which accommodates the light-guiding convex portion and the light source. The light-guiding structure is obliquely above the light source, and the light-guiding convex portion has a light incident surface. The light incident surface is inclined with respect to the central axis and configured for receiving the detection light.

In some embodiments of the present disclosure, the light-guiding structure is cup-shaped and accommodates the light source, and the light sensor is located outside the light-guiding structure.

In some embodiments of the present disclosure, the light-guiding structure has an M-shaped cross section.

In some embodiments of the present disclosure, the optical detection apparatus includes a plurality of the light sources and a plurality of the light sensors, in which each light source and each light sensor are located at the two opposite sides of the central axis.

In some embodiments of the present disclosure, the optical detection apparatus includes a plurality of the light sources and a plurality of the light sensors, and the light sources are among the light sensors.

In some embodiments of the present disclosure, the optical detection apparatus comprises a plurality of the light sources and a plurality of the light sensors, in which the light sources are centrosymmetric with respect to the central axis, and the light sensors are centrosymmetric with respect to the central axis.

In some embodiments of the present disclosure, the light-guiding structure has a height smaller than or equal to 100 um.

In some embodiments of the present disclosure, the light resource comprises a blue source, a green light source, or a red light source.

In some embodiments of the present disclosure, the light source comprises a mini light emitting diode or a micro light emitting diode.

In embodiments of the present disclosure, an optical detection apparatus is provided, and the optical detection apparatus a unique light-guiding structure. The light-guiding structure is configured to deflect the detection light from a side relative to a central axis of the light-guiding structure to another side thereof. In respect with light-guiding structure, a light source and a light sensor are respectively disposed at two different sides relative to the central axis. Therefore, the detection accuracy of the optical detection apparatus is improved, so as to adjust the passing path of the detection light and decrease the volume of the optical detection apparatus.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
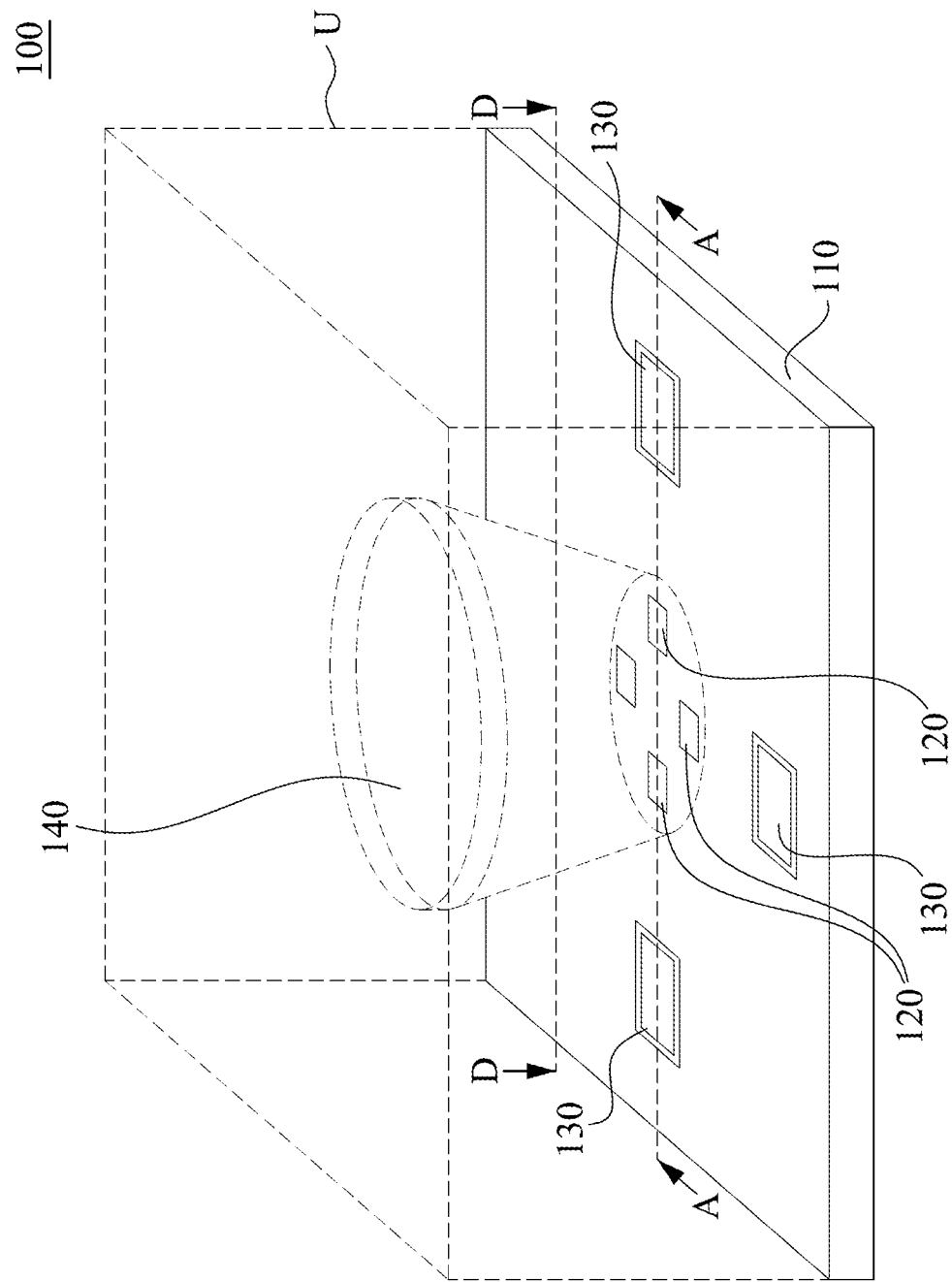
FIG. 1 illustrates a schematic view of an optical detection apparatus in accordance with some embodiments of the present disclosure.

Reference will now be made in detail to the present embodiments of the invention, examples of which are illustrated in the accompanying drawings. Wherever possible, the same reference numbers are used in the drawings and the description to refer to the same or like parts.

Reference is made to FIG. 1. FIG. 1 illustrates a schematic view of an optical detection apparatus 100 in accordance with some embodiments of the present disclosure. The optical detection apparatus 100 includes a substrate 110, a light source 120, a light sensor 130, and a light-guiding structure 140. In some embodiments of the present disclosure, the light source 120 is configured to generate detection light, and the detection light is deflected by the light-guiding structure 140 to be projected on an object 200 such as human skin under test, such that the detection light which is further reflected by the object 200 can be received by the light sensor 130. Moreover, the optical detection apparatus 100 further includes a housing U, in which the housing U accommodates and protects the light source 120, the light sensor 130, and the light-guiding structure 140. In addition, the housing U can be made from a transparent material. The present disclosure is not limited in this respect.

Specifically, the substrate 110 can be a transparent substrate or a translucent substrate. For instance, the substrate 110 is a rigid substrate, a flexible substrate, a glass substrate, a sapphire substrate, a silicon substrate, a printed circuit board, a metal substrate, or a ceramic substrate. The present disclosure is not limited in this respect. Moreover, the light source 120 can include a blue light source, a green light source, a red light source, or an infrared light source, and the light source 120 can include a light-emitting diode (LED), such as an organic light-emitting diode (OLED), a mini light-emitting diode (mini LED), a micro light-emitting diode (micro LED), and so on. The present disclosure is not limited in this respect. In some embodiments of the present disclosure, the light sensor 130 is corresponding to a light frequency which is generated from the light source 120. When the light source 120 includes a red light source and/or an infrared light source, the light sensor 130 has a red light sensor and/or an infrared light sensor, so as to detect blood oxygen saturation level. Moreover, when the light source 120 is a green light source, the light sensor 130 has a corresponding green light sensor, so as to detect human pulses. Specifically, the light sensor 130 can include a photodiode junction detector, a photomultiplier (PMT), a charge coupled device (CCD), or a complementary metal-oxide semiconductor (CMOS) sensor. The present disclosure is not limited in this respect. Specifically, the light-guiding structure 140 can include a transparent glass or a transparent polymer. The present disclosure is not limited in this respect.

Figure 2:
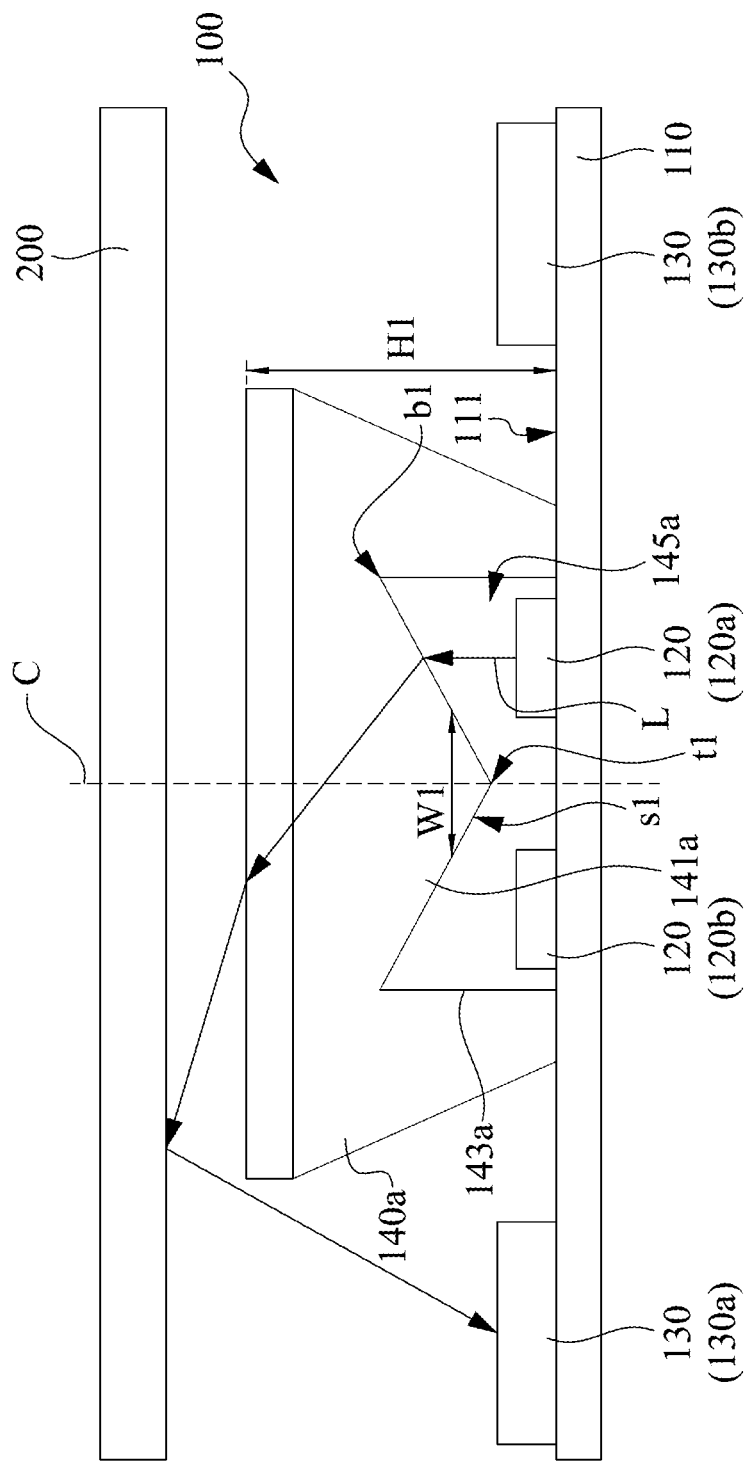
FIGS. 2-6 respectively illustrate cross section views of the optical detection apparatus 100 of FIG. 1 in accordance with some embodiments of the present disclosure.

Reference is made to FIG. 2. FIG. 2 illustrates a cross section view of the optical detection apparatus 100 taken from a section line A in FIG. 1 in accordance with some embodiments of the present disclosure. In some embodiments of the present disclosure, the optical detection apparatus 100 includes a substrate 110, a light source 120, a light sensor 130, and a light-guiding structure 140a, and the substrate 110 has a top surface 111. The light source 120 is located on the top surface 111, and the light source 120 is configured to generate detection light L moving toward an object 200 such as human skin above the light source 120. The light sensor 130 is located on the top surface 111. The light-guiding structure 140a is above the top surface 111 and at least partially above the light source 120. A central axis C which passes through a center of the light-guiding structure 140a is vertical to the top surface 111, and the light-guiding structure 140a is symmetric with respect to the central axis by reflection symmetry or central symmetry. The light source 120 and the light sensor 130 are located at two opposite sides relative to the central axis C, and the light-guiding structure 140a is configured to deflect the detection light L which comes from one of the two opposite sides at which the light source 120 is located to move toward another one of the two opposite sides at which the light sensor 130 is located. Therefore, the object 200 reflects the detection light L, so as to project the detection light L on the light sensor 130. The present disclosure is not limited in this respect.

In some embodiments of the present disclosure, the optical detection apparatus 100 includes a first light source 120a, a second light source 120b, a first light sensor 130a, and a second light sensor 130b. The first light source 120a and the first light sensor 130a are located at two opposite sides relative to the central axis C, thus the central axis C is located between the first light source 120a and the first light sensor 130a. The detection light L generated by the first light source 120a is deflected to a surface of the object 200, and then the object 200 reflects the detection light L to move toward the first light sensor 130a. Therefore, the first light sensor 130a and the second light sensor 130b can efficiently receive light, so as to improve the detection accuracy of the optical detection apparatus 100. In order to miniaturize the optical detection apparatus 100, it is benefit to deflect the passing path of the detection light L.

Similarly, the second light source 120b and the second light sensor 130b are located at two opposite sides relative to the central axis C, thus the central axis C is located between the second light source 120b and the second light sensor 130b. The detection light L generated by the second light source 120b would be deflected by the light-guiding structure 140a, and then the object 200 reflects the detection light L to move toward the second light sensor 130b. Therefore, the second light sensor 130b can efficiently receive light.

In some embodiments of the present disclosure, a straight line such as the cross section line A in FIG. 1 can passes through the first light source 120a, the second light source 120b, the first light sensor 130a and the second light sensor 130b. Therefore, the first light source 120a, the second light source 120b, the first light sensor 130a, and the second light sensor 130b occupy very small space of the optical detection apparatus 100, so as to miniaturize the optical detection apparatus 100. The present disclosure is not limited in this respect.

In some embodiments of the present disclosure, the light-guiding structure 140a includes a light-guiding convex portion 141a which has a light incident surface s1 inclined with respect to the central axis C. The light-guiding convex portion 141a is defined between a bottom end portion t1 and a top edge portion b1 thereof, and a straight line which extends from the bottom end portion t1 to the top edge portion b1 is inclined with respect to central axis C. The light incident surface s1 is configured for receiving the detection light L, and the detection light L enters the light-guiding convex portion 141a from the light incident surface s1, such that the light-guiding structure 140a further deflects the detection light L. Specifically, the light-guiding convex portion 141a is cone-shaped. For instance, the light-guiding convex portion 141a is a circular cone, a triangular cone, quadrangular cone, or any suitable polygonal cone. The light-guiding convex portion 141a has a width W1 which gradually decreases toward the substrate 110, and the light incident surface s1 can be flat or curved. The present disclosure is not limited in this respect.

In some embodiments of the present disclosure, the light-guiding structure 140a has the light-guiding convex portion 141a, a sidewall 143a, and a lower recess portion 145a, in which the sidewall 143a surrounds the light-guiding convex portion 141a and the light source 120, so as to form the lower recess portion 145a. In other words, the light-guiding convex portion 141a and the sidewall 143a collectively form and define the lower recess portion 145a. Moreover, the lower recess portion 145 accommodates the light source 120 and the light-guiding convex portion 141a, and the light-guiding convex portion 141a is obliquely above the light source 120, such that the light incident surface s1 of the light-guiding convex portion 141a can efficiently receive the detection light L. The present disclosure is not limited in this respect. In FIG. 2, the light-guiding convex portion 141a and the sidewall 143a collectively form an M-shaped cross section, and the light-guiding structure 140a has an M-shaped outline. In some embodiments of the present disclosure, the light-guiding structure 140a is cup-shaped. The light-guiding structure 140a accommodates the light source 120, but the light sensor 130 is outside the light-guiding structure 140a. In addition, the light-guiding structure 140a has a height H1 which is equal to or smaller than 100 um. Therefore, the volume of the optical detection apparatus 100 can be decreased, so as to adjust the passing path of the detection light L. In some embodiments, the light-guiding structure 140a has a height H1 which is equal to or smaller than 75 um. The present disclosure is not limited in this respect.

Figure 3:
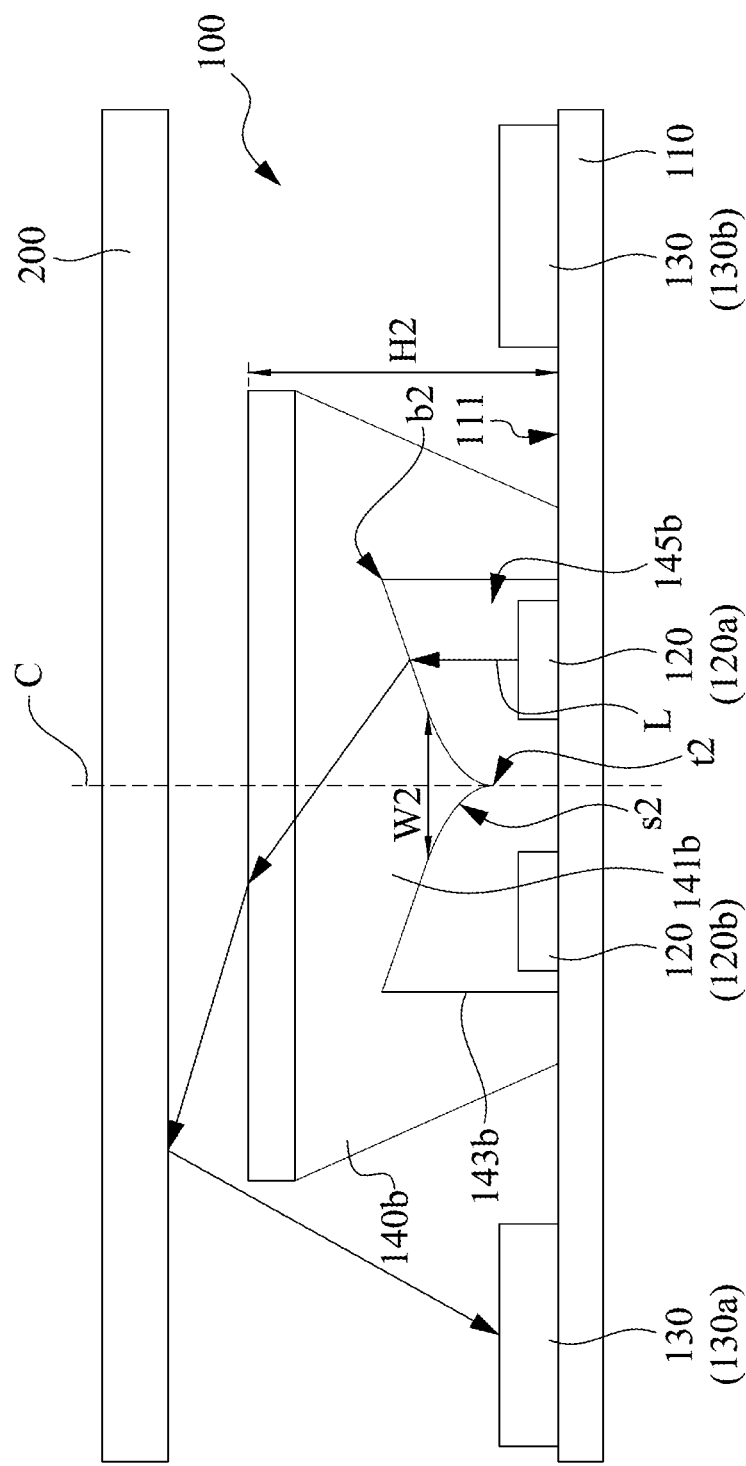

Reference is made to FIG. 3. FIG. 3 illustrates a cross section view of the optical detection apparatus 100 taken from the cross section line A in FIG. 1 in accordance with some embodiments of the present disclosure. FIGS. 2 & 3 are substantially the same, and the light-guiding structure 140a in FIG. 2 is different from a light-guiding structure 140b in FIG. 3. Therefore, the similar details are not repeated in the present disclosure. In some embodiments of the present disclosure, the light-guiding structure 140b has a light-guiding convex portion 141b, and the light-guiding convex portion 141b has a light incident surface s2 which is inclined with respect to central axis C. The light-guiding convex portion 141b is defined between a bottom end portion t2 and a top edge portion b2 thereof, and a straight line passing through the bottom end portion t2 and the top edge portion b2 is inclined with respect to the central axis C. The light incident surface s2 is configured for receiving the detection light L, and the detection light L enters the light-guiding convex portion 141b from the light incident surface s2 enters, such that the light-guiding structure 140b can deflect the detection light L. Specifically, the light-guiding convex portion 141b is cone-shaped, and the light-guiding convex portion 141b has a width W2 which gradually decrease toward substrate 110. Moreover, the light incident surface s2 is a curved concave surface. The present disclosure is not limited in this respect.

In some embodiments of the present disclosure, the light-guiding structure 140b has the light-guiding convex portion 141b, a sidewall 143b, and a lower recess portion 145b, and the sidewall 143b surrounds the light-guiding convex portion 141b and the light source 120, so as to form the lower recess portion 145b. In other words, the light-guiding convex portion 141b and the sidewall 143b collectively form and define the lower recess portion 145b. In FIG. 3, the light-guiding convex portion 141b and the sidewall 143b collectively form an M-shaped cross section, thus the light-guiding structure 140b has an M-shaped outline. In some embodiments of the present disclosure, the light-guiding structure 140b is cup-shaped. The light-guiding structure 140b accommodates the light source 120, but the light sensor 130 is located outside the light-guiding structure 140b. In addition, the light-guiding structure 140b has a height H2 which is equal to or smaller than 100 um. Therefore, the volume of the optical detection apparatus 100 can be decreased, so as to adjust the passing path of the detection light L. In some embodiments of the present disclosure, the light-guiding structure 140b has a height H2 equal to or smaller than 75 um. The present disclosure is not limited in this respect.

Figure 4:
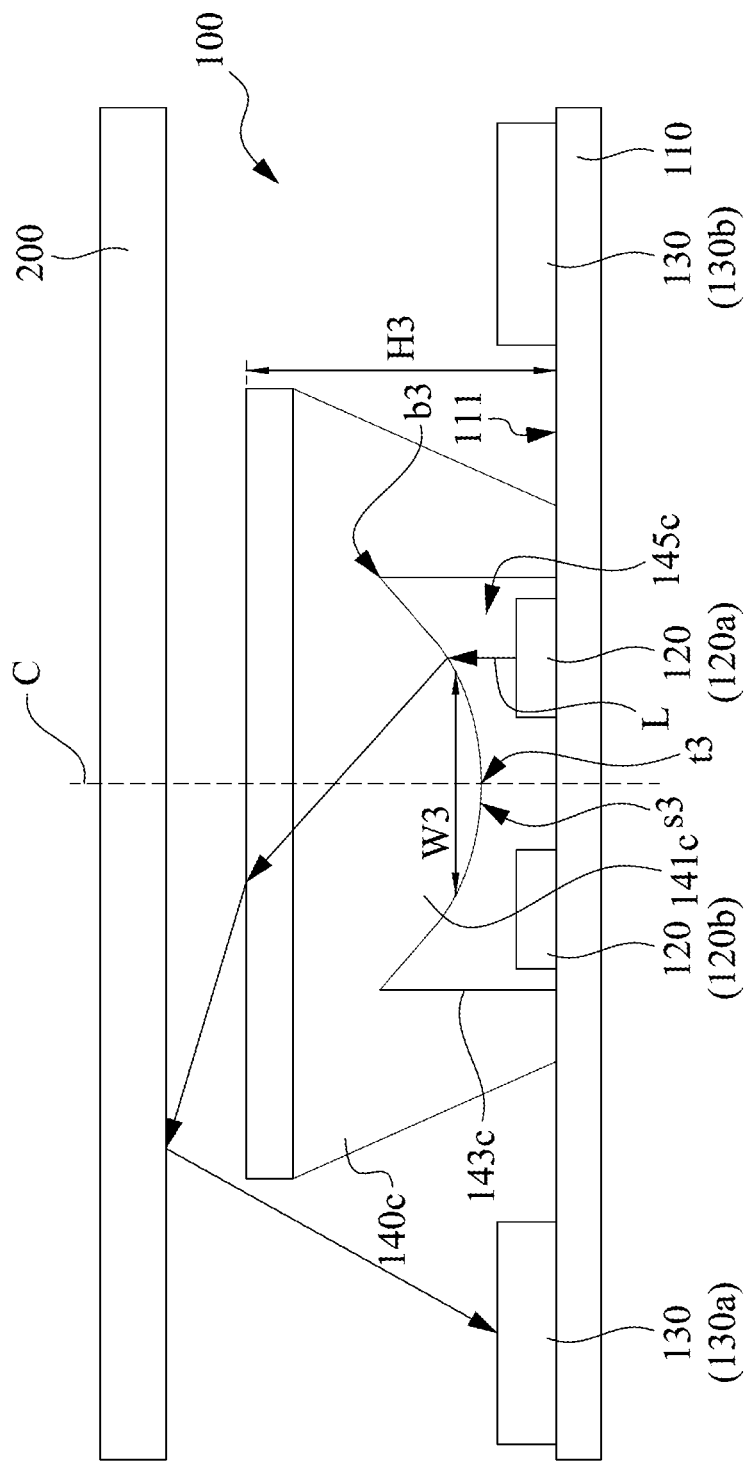

Reference is made to FIG. 4. FIG. 4 illustrates a cross section view of the optical detection apparatus 100 taken from the cross section line A in FIG. 1 according to some embodiments of the present disclosure. FIG. 4 and FIG. 2 are substantially the same, but a light-guiding structure 140c of the optical detection apparatus 100 in FIG. 4 is different from the light-guiding structure 140a in FIG. 2. Therefore, the similar details are not repeated in the present disclosure. In some embodiments of the present disclosure, the light-guiding structure 140c has a light-guiding convex portion 141c which is circular-arc shaped, and the light-guiding convex portion 141c is inclined with respect to a light incident surface s3 of the central axis C. The light-guiding convex portion 141c is defined between a bottom end portion t3 and a top edge portion b3 thereof, and a straight line which passes through the bottom end portion t3 and the top edge portion b3 is inclined with respect to the central axis C. The light incident surface s3 is configured to receive the detection light L, and the detection light L enters the light-guiding convex portion 141c from the light incident surface s3, such that the light-guiding structure 140c can deflect the detection light L. Specifically, the light-guiding convex portion 141c is circular-arc-shaped, and the light-guiding convex portion 141 has a width W3 which gradually decreases toward the substrate 110, and the light incident surface s3 is a curved convex surface. The present disclosure is not limited in this respect.

In some embodiments of the present disclosure, the light-guiding structure 140c has the light-guiding convex portion 141c, a sidewall 143c, and a lower recess portion 145c, and the sidewall 143c surrounds the light-guiding convex portion 141c and the light source 120 to form the lower recess portion 145c. In other words, the light-guiding convex portion 141c and the sidewall 143c collectively form and define the lower recess portion 145c. In FIG. 4, the light-guiding convex portion 141 and the sidewall 143c collectively form an M-shaped cross section, and the light-guiding structure 140c has an M-shaped outline. In some embodiments of the present disclosure, the light-guiding structure 140c is cup-shaped, and the light-guiding structure 140c accommodates the light source 120. On the other hand, the light sensor 130 is located outside the light-guiding structure 140c, and the light-guiding structure 140c has a width H3 which is equal to or smaller than 100 um. The volume of the optical detection apparatus 100 can be decreased, so as to adjust the passing path of the detection light L. In some embodiments, the light-guiding structure 140c has a height H3 equal to or smaller than 75 um. The present disclosure is not limited in this respect.

Figure 5:
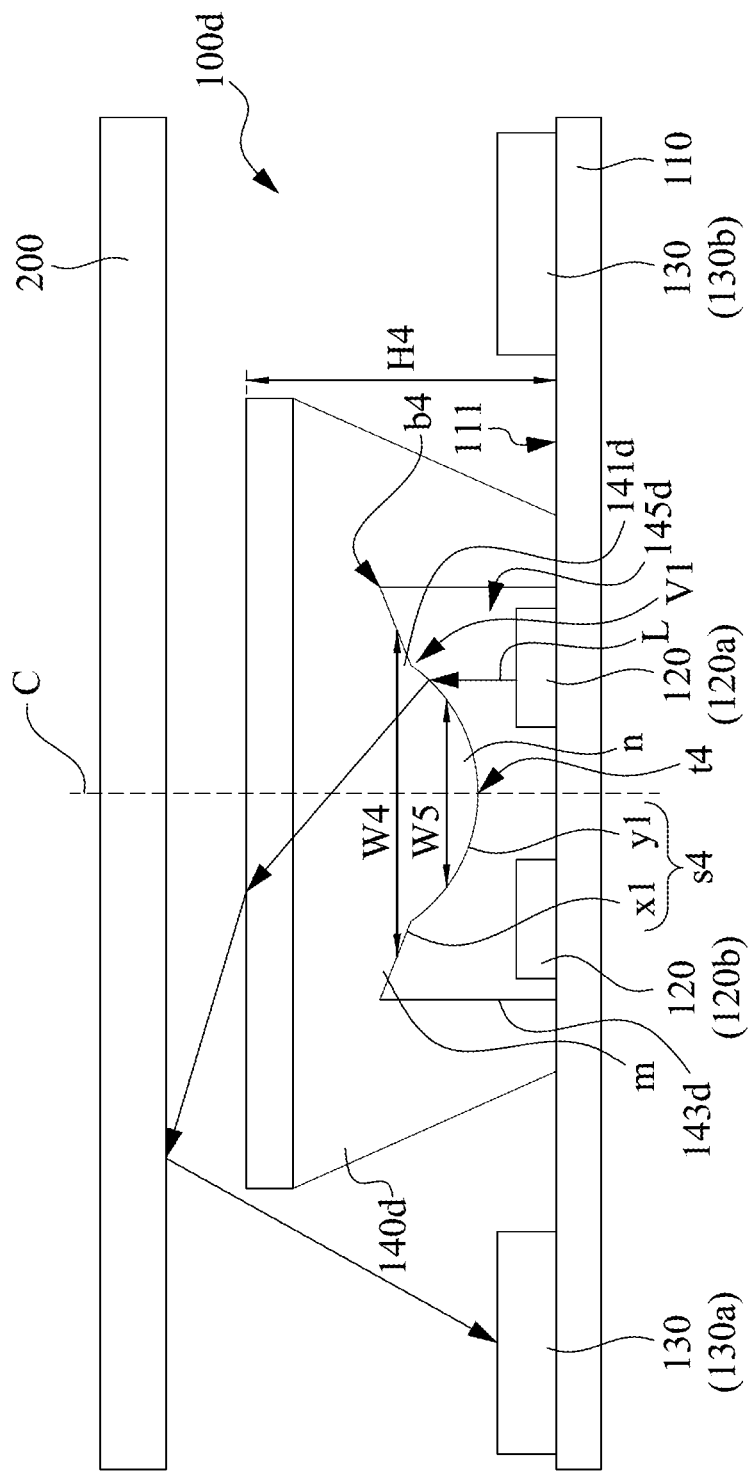

Reference is made to FIG. 5. FIG. 5 illustrates a cross section view of the optical detection apparatus 100 taken from the cross section line A in FIG. 1. FIG. 2 and FIG. 5 are substantial the same, but a light-guiding structure 140d of the optical detection apparatus 100 in FIG. 5 is different from the light-guiding structure 140a in FIG. 2. Therefore, the similar details are not repeated in the present disclosure. In some embodiments of the present disclosure, the light-guiding structure 140d has the a light-guiding convex portion 141d, the light-guiding convex portion 141d has a light incident surface s4 which is inclined with respect to the central axis C. The light-guiding convex portion 141d is defined between a bottom end portion t4 and a top edge portion b4, and a straight line pasting through the bottom end portion t4 and the top edge portion b4 is inclined with respect to the central axis C. The light incident surface s4 is configured for receiving the detection light L, and the detection light L enters the light-guiding convex portion 141d from the light incident surface s4, such that the light-guiding structure 140d deflects the detection light L. Specifically, the light-guiding convex portion 141d has a column portion m and a curved convex portion n under the column portion m, and the column portion m can be a triangular column, a quadrangular column, a pentagonal column, a hexagonal column, an octagonal column, or a cylinder. The column portion m is connected to and located on the curved convex portion n. The column portion m has a flat surface x1, and the curved convex portion n has a curved surface y1. The flat surface x1 and the curved surface y1 collectively form the light incident surface s4. Moreover, there is a curvature inversion point V1 on the light incident surface s4, and the curvature inversion point V1 is at the position where column portion m joins the curved convex portion n. More specifically, the curvature inversion point V1 is at a position where the flat surface x1 joins the curved surface y1. Moreover, a width W4 of the column portion m gradually decreases toward the substrate 110, and a width W5 of the curved convex portion n gradually decreases toward the substrate 110. The width W4 of the column portion m is equal to or greater than the width W5 of the curved convex portion n. The present is not disclosed in this respect.

In some embodiments of the present disclosure, the light-guiding structure 140d has the light-guiding convex portion 141d, a sidewall 143d, and the lower recess portion 145d, in which the sidewall 143d surrounds the light-guiding convex portion 141d and the light source 120 to form the lower recess portion 145d. Therefore, the light-guiding convex portion 141d and the sidewall 143d collectively form and define the lower recess portion 145d. In FIG. 5, the light-guiding convex portion 141d and the sidewall 143d collectively form an M-shaped cross section, and the light-guiding structure 140d has an M-shaped outline. In some embodiments of the present disclosure, the light-guiding structure 140d is cup-shaped, the light-guiding structure 140d accommodates the light source 120, and the light sensor 130 is located outside the light-guiding structure 140d. Moreover, the light-guiding structure 140d has a width H4 which is equal to or smaller than 100 um. The volume of the optical detection apparatus 100 can be decreased, so as to adjust the passing path of the detection light L. In some embodiments, the light-guiding structure 140d has a height H4 equal to or smaller than 75 um.

Figure 6:
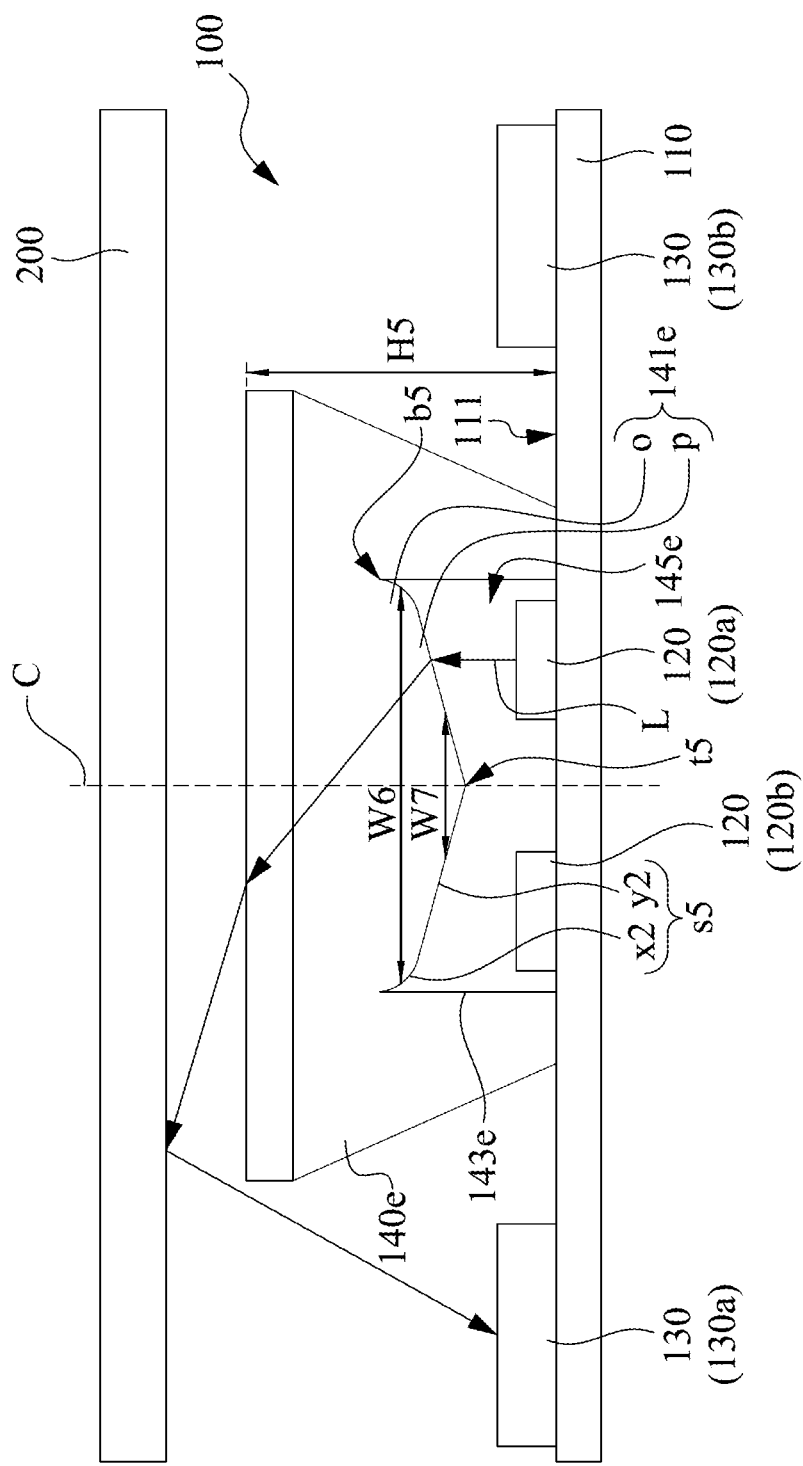

Reference is made to FIG. 6. FIG. 6 illustrates a cross section view of the optical detection apparatus 100 taken from the cross section line A in FIG. 6. FIG. 2 and FIG. 6 are substantially the same, but a light-guiding structure 140e of the optical detection apparatus 100 in FIG. 6 is different from the light-guiding structure 140a in FIG. 2. Therefore, the similar details are not repeated in the present disclosure. In some embodiments of the present disclosure, the light-guiding structure 140e has the light-guiding convex portion 141e, and the light-guiding convex portion 141e has a light incident surface s5 which inclined with respect to the central axis C. The light-guiding convex portion 141e is defined between a bottom end portion t5 and a top edge portion b5 thereof, and a straight line passing through the bottom end portion t5 and the top edge portion b5 is inclined with respect to the central axis C. The light incident surface s5 is configured for receiving the detection light L, and the detection light L enters the light-guiding convex portion 141e from the light incident surface s5, such that the light-guiding structure 140e can deflect the detection light L.

Specifically, the light-guiding convex portion 141e has a column portion o and a cone portion p, and the column portion o can be a triangular column, quadrangular column, a pentagonal column, a hexagonal column, an octagonal column or a cylinder. The present disclosure is not limited in this respect. The cone portion p which is corresponding to the column portion o can be a triangular cone, a quadrangular pyramid, a pentagonal cone, a hexagonal cone, an octagonal cone, or a circular cone. The column portion o is connected to and located on the cone portion p. The column portion o has a curved convex surface x2, and the cone portion p has a flat surface y2. The curve convex surface x2 and the flat surface y2 collectively form a light incident surface s5. Moreover, the column portion o has a width W6 which gradually decreases toward the substrate 110, and the cone portion p has a width W7 which gradually decreases toward the substrate 110. The width W6 of the column portion o is equal to or greater than a width W7 of the cone portion p. The present disclosure is not limited in this respect.

In some embodiments of the present disclosure, the light-guiding structure 140e has the light-guiding convex portion 141e, a sidewall 143e, and a lower recess portion 145e. The sidewall 143e surrounds the light-guiding convex portion 141e and the light source 120 to form the lower recess portion 145e. In other words, the light-guiding convex portion 141e and the sidewall 143e collectively form and define the lower recess portion 145e. In FIG. 6, the light-guiding convex portion 141e and the sidewall 143e collectively form an M-shaped cross section, and the light-guiding structure 140e has an M-shaped outline. In some embodiments of the present disclosure, the light-guiding structure 140e is cup-shaped, and the light source 120 is accommodated in the light-guiding structure 140e. On the other hand, the light sensor 130 is located outside the light-guiding structure 140e. Moreover, the light-guiding structure 140e has a height H2 which is equal to or smaller than 100 um. Therefore, the volume of the optical detection apparatus 100 can be decreased, so as to adjust the passing path of the detection light L. In some embodiments, the light-guiding structure 140d has a height H5 which is equal to or smaller than 75 um.

Figure 7:
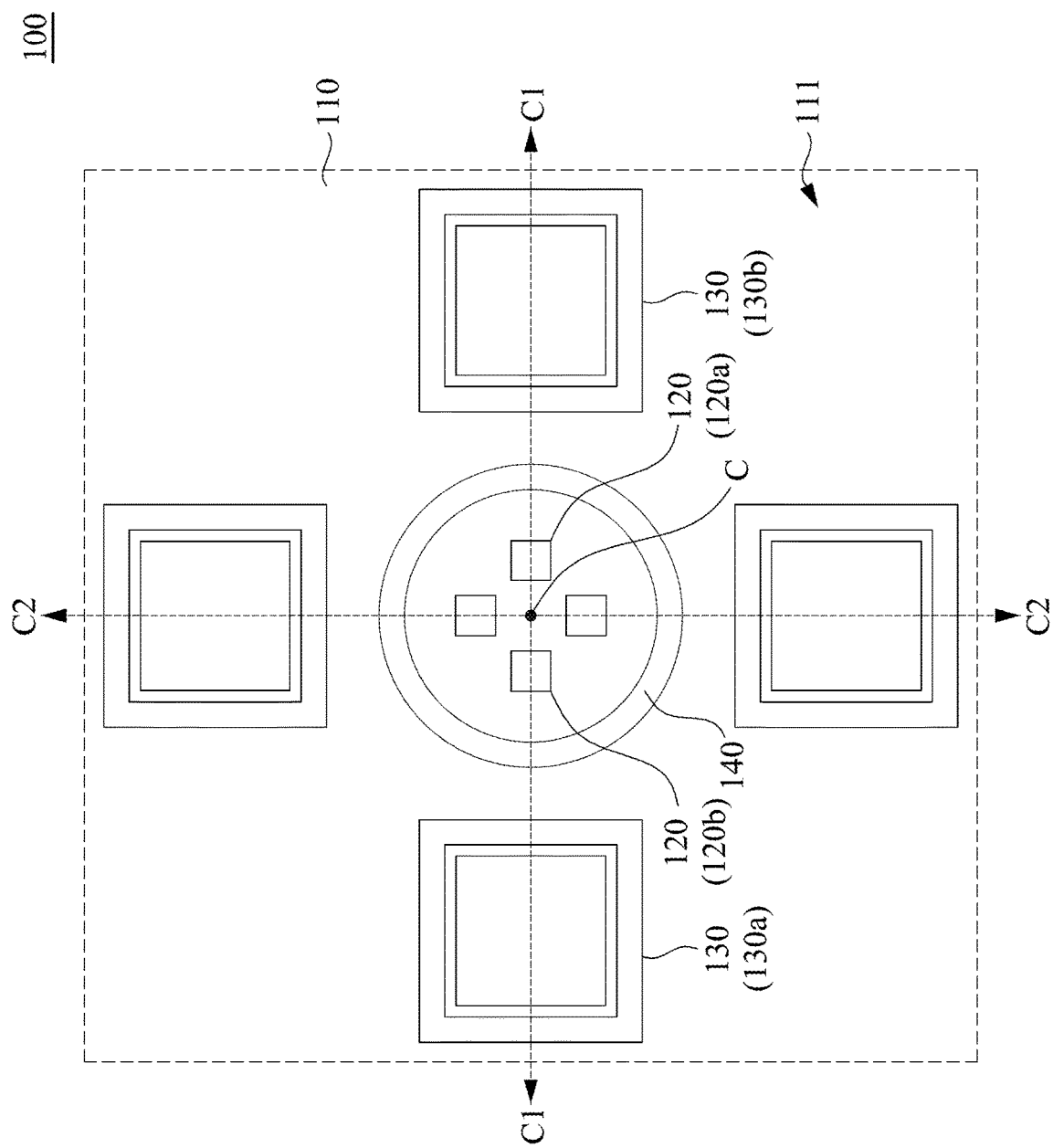
FIGS. 7-10 respectively illustrate top views of the optical detection apparatus of FIG. 1 in accordance with some embodiments of the present disclosure.

Reference is made to FIG. 7. FIG. 7 illustrates a top view of the optical detection apparatus 100 in FIG. 1 taken from a vertical position D. In some embodiments of the present disclosure, the optical detection apparatus 100 includes a plurality of the light sources 120 such as four light sources 120 and a plurality of the light sensors 130 such as four light sensors 130. The light sources 120 surround the central axis C, and the light sensors 130 surrounds the central axis C and the light sources 120. Therefore, the light sources 120 are among the light sensors 130, and the central axis C does not pass any light source 120. Specifically, the light sensors 130 are respectively opposite to the light sources 120 with respect to the central axis C, and the light sources 120 and the light sensors 130 are centrosymmetric with respect to the central axis C. That is, the locations of the four light sources 120 are centrosymmetric with respect to the central axis C, and the locations of the four light sensors 130 are centrosymmetric with respect to the central axis C rather than referring to the shapes of the light sources 120 and the light sensors 130 are symmetrical.

FIG. 7 illustrate a first straight line C1 and a second straight line C2 which is vertical to the first straight line C1, in which the first straight line C1 and the second straight line C2 are vertical to the central axis C. In some embodiments of the present disclosure, four light sources 120 surround the central axis C, and four light sensors 130 surround the light sources 120 and the central axis C. The first straight line C1 passes through two light sources 120 and two light sensors 130, and the second straight line C2 passes another two light sources 120 and another two light sensors 130. Therefore, the volume of the optical detection apparatus 100 can be decreased, and the interference among the four light sources 120 can be curbed, so as to improve the detection accuracy of the optical detection apparatus 100. In other embodiments of the present disclosure, the first straight line C1 crosses the second line C2 and form an angle which is not 90 degree, thus light sources 120 and the light sensors 130 are not centrosymmetric with respect to the central axis C. The present disclosure is not limited in this respect.

Specifically, the first straight line C1 passes through a first light source 120a, a second light source 120b, a first light sensor 130a, and a second light sensor 130b, in which the first light source 120a and the second light source 120b is between the first light sensor 130a and the second light sensor 130b. The first light source 120a and the second light source 120b are inside the light-guiding structure 140, and the first light sensor 130a and the second light sensor 130b are outside the light-guiding structure 140. Similarly, the second straight line C2 passes through another two light source 120 and another two light sensors 130, in which the another two first light sources 120 are between the another two light sensors 130. The present disclosure is not limited in this respect.

Figure 8:
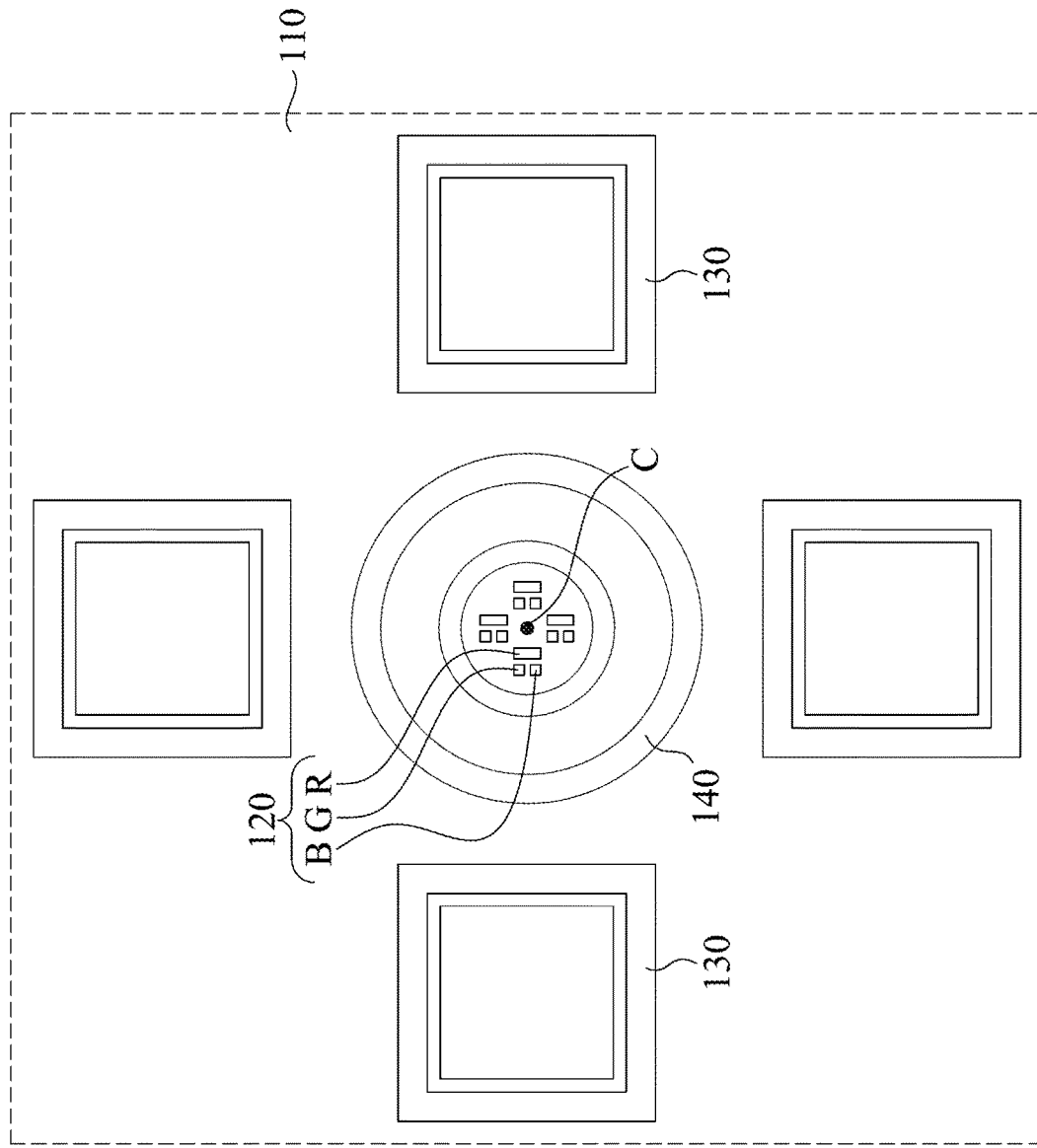

Reference is made to FIGS. 7 and 8, and the optical detection apparatus 100 shown in FIG. 7 is similar to the optical detection apparatus 100 shown in FIG. 8. FIG. 8 further shows that the light source 120 which includes a blue light source B, a green light source G, and a red light source R. In some embodiments of the present disclosure, the light source 120 further includes an infrared light source, and the present disclosure is not limited in this respect. In FIG. 8, a plurality of the light sources 120 surround the central axis C, and a plurality of the light sensors 130 surround the central axis C and the light sources 120. Therefore, the light sources 120 are among the light sensors 130, and the present disclosure is not limited in this respect. In some embodiments, the light sources 120 can generate light which has different frequency bands, such as blue light, green light, red light, and infrared light.

Figure 9:
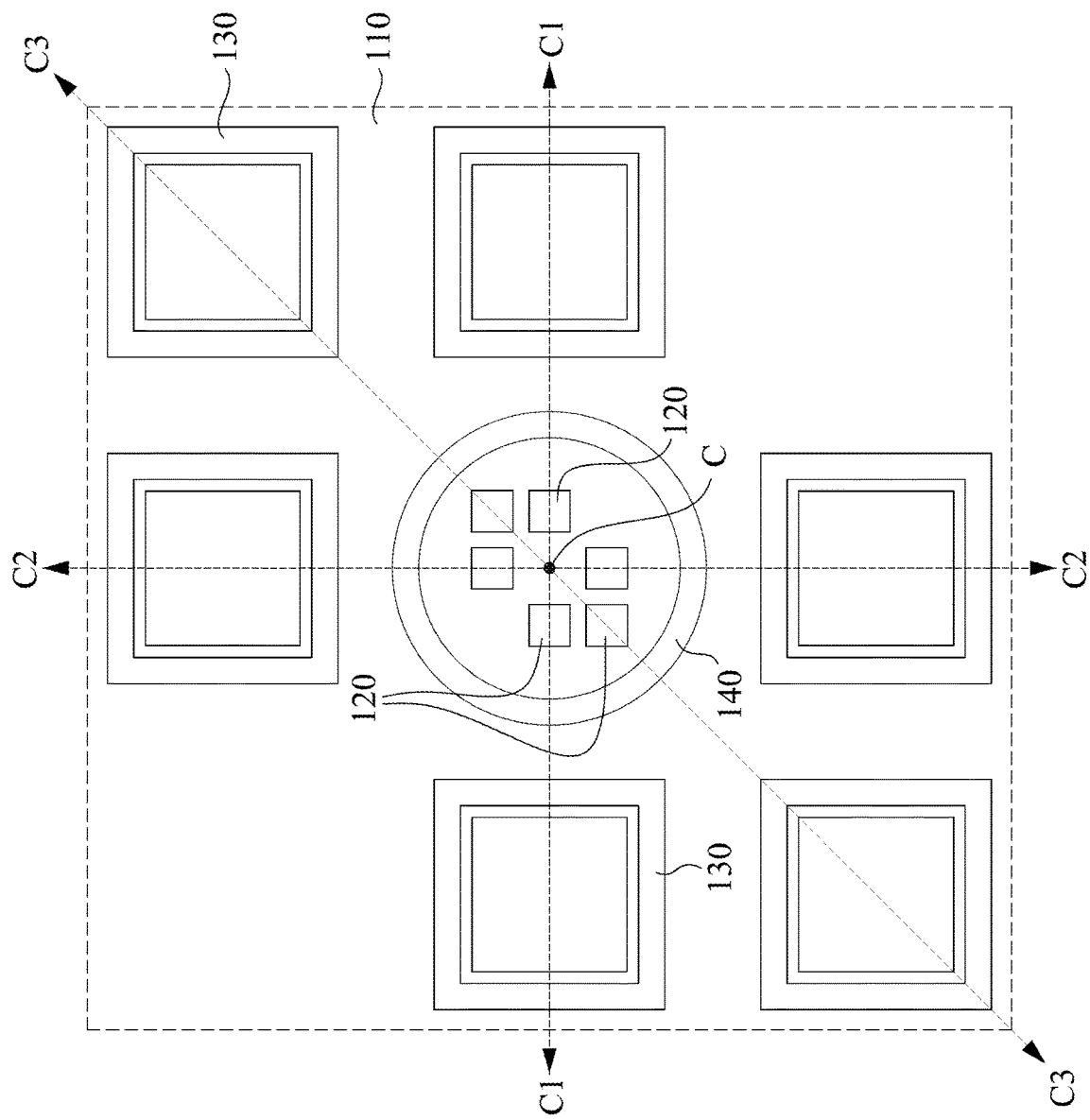

Reference is made to FIG. 9. FIG. 9 is similar to FIG. 7, and the optical detection apparatus 100 in FIG. 9 includes six light sources 120 and six light sensors 130. The six light sources 120 surround the central axis C, and the six light sensors 130 surround the central axis C and the six light sources 120. In other words, the central axis C does not pass through any light source 120. Moreover, the six light sources 120 are in the light-guiding structure 140, and the six light sensors 130 are located outside the light-guiding structure 140. The present disclosure is not limited in this respect.

In comparison with FIG. 7, FIG. 9 further illustrates a third straight line C3, and the third straight line C3 is vertical to the central axis C and crosses the first straight line C1 and the second straight line C2. The first straight line C1 and the third straight line C3 form an angle which is 45 degree, and the second straight line C2 and the third straight line C3 form an angle which is 45 degree. In some embodiments of the present disclosure, each one of the first straight line C1, the second straight line C2, and the third straight line C3 passes two of the light sources 120 and two of the light sensors 130. Specifically, the six light sources 120 and the six light sensors 130 are symmetrical with respect to the third straight line C3. That is, locations of the six light sources 120 and the six light sensors 130 are symmetrical with respect to the third straight line C3 rather than referring to the shapes of the light sources 120 and the light sensors 130 are symmetrical. Therefore, the volume of the optical detection apparatus 100 can be decreased, and interference among the light sources 120 can be curbed, so as to improve the detection accuracy of the optical detection apparatus 100. In other embodiments of the present disclosure, the third straight line C3 can form an angle in any degree with the first straight line C1 or the second straight line C2. Therefore, the light sources 120 and light sensors 130 are not symmetrical with respect to the central axis C. The present disclosure is not limited in this respect.

Figure 10:
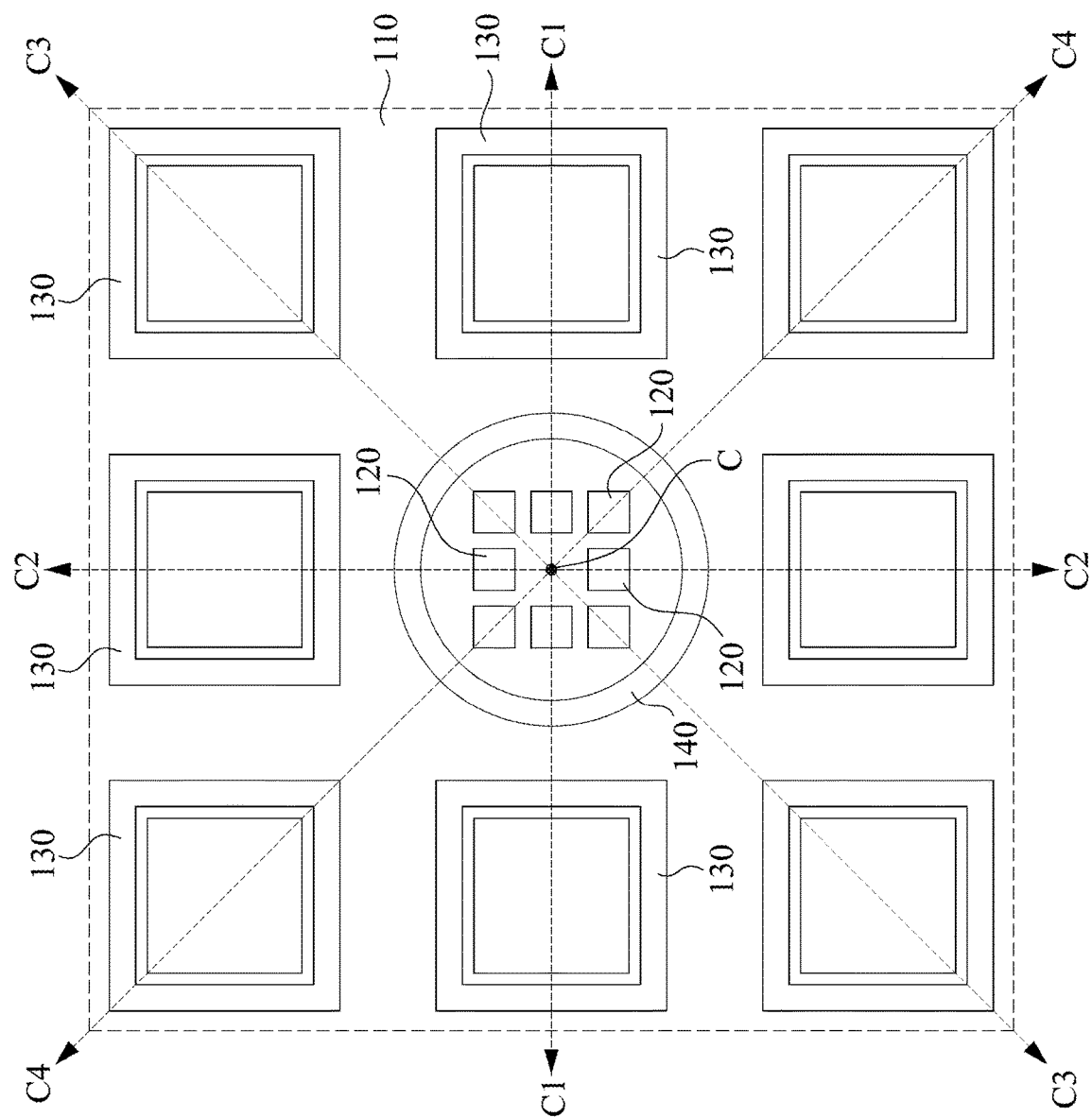

Reference is made to FIG. 10. FIG. 10 is similar to FIG. 9, and the optical detection apparatus 100 has eight light sources 120 and eight light sensors 130. The eight light sources 120 surround the central axis C, and the light sensors 130 surround the central axis C and the eight light sources 120. Therefore, the central axis C does not pass through any light source 120. Moreover, the eight light sources 120 are in the light-guiding structure 140, and the eight light sensors 130 are outside the light-guiding structure 140. The present disclosure is not limited in this respect.

In comparison with FIG. 9, FIG. 10 further illustrates a fourth straight line C4, and the fourth straight line C4 is vertical to the central axis C and the third straight line C3. In some embodiments of the present disclosure, each one of the first straight line C1, the second straight line C2, the third straight line C3, and the fourth straight line C4 passes through two of the light sources 120 and two of the light sensors 130. Moreover, the eight light sources 120 and the eight light sensors 130 are centrosymmetric with respect to the central axis C, so as to decrease the volume of the optical detection apparatus 100 and curb the interference among the light sources 120. Therefore, the detection accuracy of the optical detection apparatus 100 is improved. In some other embodiments of the present disclosure, the third straight line C3 is not vertical to the fourth straight line C4, and the eight light sources 120 and the eight light sensors 130 are not centrosymmetric with respect to the central axis C. The present disclosure is not limited in this respect.

In embodiments of the present disclosure, an optical detection apparatus is provided, and the optical detection apparatus a unique light-guiding structure. The light-guiding structure is configured to deflect the detection light from a side of a central axis of the light-guiding structure to another side thereof. In respect with light-guiding structure, a light source and a light sensor are respectively disposed at two different sides of the central axis. Therefore, the detection accuracy of the optical detection apparatus is improved, so as to adjust the passing path of the detection light and decrease the volume of the optical detection apparatus.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An optical detection apparatus comprising:
    a substrate having a top surface;
    a light source on the top surface is configured to generate detection light toward an object over the light source;
    a plurality of light sensors on the top surface and surrounding the light source; and
    a light-guiding structure above the top surface and at least partially above the light source, and a central axis of the light-guiding structure is vertical to the top surface, the light source and the light sensors are disposed at two opposite sides of the central axis, wherein the light-guiding structure is configured to deflect the detection light from one of the two opposite sides at which the light source is located to the other one of the two opposite sides at which one of the light sensors is located, such that the detection light reflected by the object moves toward the one of the light sensors.

2. The optical detection apparatus of claim 1, wherein the light-guiding structure comprises a light-guiding convex portion which has a light incident surface inclined with respect to the central axis and configured for receiving the detection light.

3. The optical detection apparatus of claim 1, wherein the light-guiding structure comprises a cone-shaped convex portion.

4. The optical detection apparatus of claim 1, wherein the light-guiding structure comprises a circular-arc-shaped convex portion.

5. The optical detection apparatus of claim 1, wherein the light-guiding structure comprises a column portion and a curved convex portion under the column portion.

6. The optical detection apparatus of claim 1, wherein the light-guiding structure comprises a column portion and a cone portion under the column portion.

7. The optical detection apparatus of claim 1, wherein the light-guiding structure comprises a light-guiding convex portion and a lower recess portion which accommodates the light-guiding convex portion and the light source, the light-guiding convex portion is obliquely above the light source, and the light-guiding convex portion has a light incident surface inclined with respect to the central axis and configured for receiving the detection light.

8. The optical detection apparatus of claim 1, wherein the light-guiding structure is cup-shaped and accommodates the light source, and the light sensors are disposed outside the light-guiding structure.

9. The optical detection apparatus of claim 1, wherein the light-guiding structure has an M-shaped cross section.

10. The optical detection apparatus of claim 1 comprising a plurality of the light sources, wherein each light source and each light sensor are located at the two opposite sides of the central axis.

11. The optical detection apparatus of claim 1 comprising a plurality of the light sources, wherein the light sources are disposed among the light sensors.

12. The optical detection apparatus of claim 1 comprising a plurality of the light sources, wherein the light sources are centrosymmetric with respect to the central axis, and the light sensors are centrosymmetric with respect to the central axis.

13. The optical detection apparatus of claim 1, wherein the light-guiding structure has a height smaller than or equal to 100 um.

14. The optical detection apparatus of claim 1, wherein the light source comprises a blue source, a green light source, or a red light source.

15. The optical detection apparatus of claim 1, wherein the light source comprises a mini light emitting diode or a micro light emitting diode.

* * * * *